United States Patent [19]

Wasley

[11] 4,424,221
[45] Jan. 3, 1984

[54] METHOD OF TREATING ANXIETY

[75] Inventor: Jan W. F. Wasley, Chatham, N.J.

[73] Assignee: Ciba-Geigy Corporation, Ardsley, N.Y.

[21] Appl. No.: 426,424

[22] Filed: Sep. 28, 1982

[51] Int. Cl.³ .......................................... A61K 31/495
[52] U.S. Cl. ................................................. 424/250
[58] Field of Search ........................................ 424/250

[56] References Cited

U.S. PATENT DOCUMENTS

| | | | |
|---|---|---|---|
| 4,128,641 | 12/1978 | Itil | 424/250 |
| 4,284,559 | 7/1981 | van der Burg | 424/250 |
| 4,316,900 | 2/1982 | Wasley | 424/274 |
| 4,333,935 | 1/1982 | van der Burg | 424/250 |

OTHER PUBLICATIONS

Dis. Nerv. Systs. 35, 10 (1974); pp. 10, 14 and 15 only enclosed.
J. Int. Med. Res. 7, 285 (1979).
Br. J. Chin. Pharmac. 5, 81S–99S (1978).

*Primary Examiner*—Stanley J. Friedman
*Attorney, Agent, or Firm*—Norbert Gruenfeld

[57] ABSTRACT

Certain 1,3,4,14b-tetrahydro-2H,10H-pyrazino[1,2-a]pyrrolo-[2,1-c][1,4]benzodiazepines e.g. those of the formula

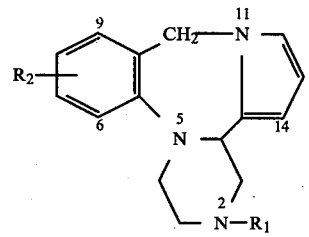

wherein $R_1$ is lower alkyl or hydroxy(lower)alkyl; $R_2$ is hydrogen, chloro or trifluoromethyl; pharmaceutically acceptable salts thereof, and pharmaceutical compositions comprising said compounds, are useful for the treatment of anxiety in mammals.

7 Claims, No Drawings

METHOD OF TREATING ANXIETY

SUMMARY OF THE INVENTION

The present invention relates to certain 1,3,4,14b-tetrahydro-2H,10H-pyrazino[1,2-a]pyrrolo[2,1-c][1,4]benzodiazepines, of formula I below, and disclosed in U.S. Pat. No. 4,316,900 granted to the Applicant, which have now been found of particularly useful antianxiety (or anxiolytic) agents suitable for the treatment of anxiety syndromes.

The present invention is specifically directed to a novel method of controlling and treating anxiety in mammals which comprises the enteral or parenteral, preferably oral, administration of an anxiolytic compound or of a pharmaceutical composition comprising an effective amount of an anxiolytic compound of formula I

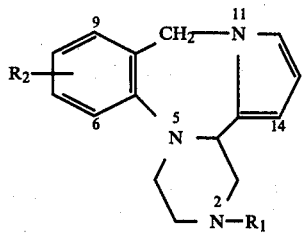

wherein $R_1$ is hydrogen, lower alkyl, lower alkenyl, cyclopropyl(lower)alkyl, lower alkanoyloxy(lower)alkyl or hydroxy-(lower)alkyl; $R_2$ is hydrogen, halogen or trifluoromethyl; and pharmaceutically acceptable salts thereof, in combination with one or more pharmaceutical carriers.

Preferred as anxiolytic agents are the compounds of formula I wherein $R_1$ is alkyl, alkenyl or hydroalkyl with up to 4 carbon atoms; $R_2$ is hydrogen, chloro, fluoro or trifluoromethyl; and pharmaceutically acceptable acid-addition salts thereof. Further preferred as anxiolytic agents are the compounds of formula I wherein $R_1$ is methyl, allyl, hydroxyethyl; $R_2$ is hydrogen, or 7-(chloro, fluoro or trifluoromethyl); and hydrochloric, fumaric and maleic acid addition salts thereof.

Particularly preferred are the anxiolytic compounds of formula I wherein $R_1$ is methyl, allyl or hydroxyethyl and $R_2$ is hydrogen.

Preferred in context of the present invention is the method of treating or controlling anxiety comprising the enteral administration of the above-preferred anxiolytic compounds or pharmaceutical compositions comprising said preferred compounds described above.

The term "lower", referred to above or hereinafter in connection with organic radicals or compounds respectively defines such with up to 7, preferably up to 4, and advantageously those with one or two carbon atoms.

The compounds of formula I above and the pharmaceutically acceptable salts thereof, their properties, methods of preparation and pharmaceutical compositions comprising said compounds are disclosed in U.S. Pat. No. 4,316,900.

Said U.S. Pat. No. 4,316,900 is furthermore directed to the useful antidepressant properties of the compounds of the invention. Analgesic, antihistaminic and antiserotoninergic properties have in addition been disclosed in the substantially equivalent European Pat. No. 1585.

Pharmaceutically acceptable salts of the compounds of instant formula I are preferably the acid-addition salts, e.g. the hydrochloride, sulfate, phosphate, maleate, fumarate and methanesulfonate (mesylate) salts; most preferred are the hydrochloride, maleate and fumarate salts.

The compounds of formula I are formulated into anxiolytic pharmaceutical compositions comprising an effective amount of a said compound of formula I or salt thereof in combination with conventional excipients or carriers suitable for either enteral or parenteral, such as oral, rectal or intravenous administration. Preferred are tablets, dragees and gelatin capsules comprising the active ingredient together with (a) diluents, e.g., lactose, dextrose, sucrose, mannitol, sorbitol, cellulose, calcium phosphates and/or glycine; (b) lubricants, e.g., silica, talcum, stearic acid, its magnesium or calcium salt and/or polyethyleneglycol; for tablets also, (c) binders, e.g., magnesium aluminum silicate, starch paste, gelatin, tragacanth, methylcellulose, sodium carboxymethylcellulose and/or polyvinylpyrrolidone; if desired, (d) disintegrants, e.g., starches, agar, alginic acid or its sodium salt, or effervescent mixtures; and/or, (e) absorbents, colorants, flavors and sweeteners. Dragee or tablet cores may be provided with suitable coatings, which may be resistant to gastric juices. Coating solutions are, for example, concentrated aqueous sugar solutions, which may contain gum arabic, polyvinylpyrrolidone, polyethylene glycol, talcum and/or titanium dioxide. Said resistant coatings are obtained with lacquer solutions in organic solvents, such as shellac, acetylcellulose phthalate or hydroxypropylmethylcellulose phthalate in ethanol and the like. Dyestuffs or pigments may be added for identification of brand name and dose. Capsules are either made from hard gelatin, or they are soft, closed capsules made from gelatin and a softener, e.g., glycerin or sorbitol. The hard capsules contain either uncompressed powder mixtures, e.g., those mentioned under (a) and (b), or granulates similar to those used for tablets. In the soft capsules said active ingredients are preferably dissolved or suspended in suitable liquids, such as fatty oils, paraffins or polyethylene glycols. Suppositories are advantageously solid, fatty emulsions or suspensions, containing the active ingredient, for example, in natural or synthetic triglycerides, paraffins, waxes and/or polyethylene glycols.

Compositions for parenteral administration are preferably aqueous solutions or suspensions of said active substances, but also oily solutions or suspensions thereof, e.g., in natural or synthetic fatty oils, such as sesame oil or ethyl oleate, in suitable ampules.

Said compositions may be sterilized and/or contain adjuvants, such as preserving, stabilizing, wetting or emulsifying agents, solution promoters, salts for regulating the osmotic pressure and/or buffers. They may also contain other therapeutically valuable substances, and are prepared according to conventional mixing, granulating or coating methods respectively. They may contain from about 10 to 95%, preferably from about 20 to 70% of the active ingredient. Individual unit dosages thereof for a mammal of about 50–70 kg weight may contain preferably between about 5 and 200 mg, advantageously about 10 to 100 mg of said active ingredients.

The new method of treating anxiety can be demonstrated in animal tests, using mammals, such as rats or monkeys as test subjects. Said compositions are administered in such tests either enterally, e.g. orally or intraperitoneally, or parenterally, e.g. intravenously. The applied dosage may range between about 1 and 200 mg/kg/day, preferably between about 2 and 100 mg/kg/day, advantageously between about 5 and 50 mg/kg/day.

Anxiolytic effects are observed, for example, according to the Cook-Davidson conflict procedure, using male Wistar rats which are maintained at 80% of normal body weight by dietary-, but not water-restriction. They are trained to press a lever within a conditioning chamber, also containing a liquid dipper, a house light, a speaker and a grid-floor. Both lever and grid are connected to an electrical shock source and the chamber is situated in a sound-attenuated room in which a white noise-source is activated during testing, in order to mask any extraneous auditory cues. Each session of 47 minutes duration consists of two alternating schedules. The first is a Variable Interval (VI) schedule of 30 seconds, lasting for 5 minutes, during which a sweetened, condensed milk reinforcement is delivered following the first lever-press after an average of 30 seconds have elapsed, and a drug-induced decrement of this performance is taken as an indication of a motor deficit. Immediately following the VI-schedule both a 1000 Hz tone and a light-cue are activated, indicating the commencement of the second Fixed Ratio (FR) schedule, lasting for 2 minutes, wherein the milk reinforcement is delivered concomitant with an electric foot shock immediately following the tenth response, thereby establishing a conflict situation. The intensity of said shock ranges between 2.0 and 3.6 mA, varying with each animal, in order to adjust them to about 25–50 responses during this schedule over the entire session. A drug-induced enhancement of performance during the FR-schedule is taken as indication of antianxiety effects. This increased performance is measured by the increased number of electric foot shocks taken during six FR sessions lasting 2 minutes each.

Illustrative of the invention, 2-methyl-1,3,4,14b-tetrahydro-10H-pyrazino[1,2-a]pyrrolo[2,1-c]-[1,4]benzodiazepine maleate administered orally in aqueous solution, e.g. at a dose of 30 mg/kg to rats administered as a 0.3% solution in distilled water, increases performance in the Cook-Davidson conflict model as evidenced by an increase of the number of shocks taken from about 25 to about 174 during the FR schedule.

Accordingly, the compounds of formula I are useful for the management of a conflict situation and in the treatment of anxiety in mammals including man.

The following examples are intended to illustrate said compositions useful in the new method according to this invention, and they are not to be construed as being limitations thereon. All parts wherever given are parts by weight, and the active ingredient is preferably 2-methyl-1,3,4,14b-tetrahydro-10H-pyrazino[1,2-a]pyrrolo[2,1-c]-[1,4]benzodiazepine or a salt thereof, but may also be any other compounds encompassed by the above structural formula I, or salts thereof.

EXAMPLE 1

Preparation of 10,000 capsules each containing 20 mg of the active ingredient:

| Formula: | |
|---|---|
| 2-methyl-1,3,4-14b-tetrahydro-10H—pyrazino[1,2-a]pyrrolo[2,1-c]-[1,4]benzodiazepine monomaleate | 200.0 g |
| Lactose | 1,700.0 g |
| Talcum powder | 100.0 g |

Procedure

All the powders are passed through a screen with openings of 0.6 mm. Then the drug substance is placed in a suitable mixer and mixed first with the talcum, then with the lactose until homogenous. No. 3 capsules are filled with 200 mg, using a capsule filling machine.

EXAMPLE 2

Preparation of 10,000 tablets each containing 50 mg of the active ingredient:

| Formula: | |
|---|---|
| 2-methyl-1,3,4-14b-tetrahydro-10H—pyrazino[1,2-a]pyrrolo[2,1-c][1,4]benzodiazepine monomaleate | 500.00 g |
| Lactose | 707.00 g |
| Corn Starch | 75.00 g |
| Polyethylene glycol 6,000 | 75.00 g |
| Talcum powder | 75.00 g |
| Magnesium stearate | 18.00 g |
| Purified water | q.s. |

Procedure

All the powders are passed through a screen with openings of 0.6 mm. Then the drug substance, lactose, talcum, magnesium stearate and half of the starch are mixed in a suitable mixer. The other half of the starch if suspended in 40 ml of water and the suspension added to the boiling solution of the polyethylene glycol in 150 ml of water. The paste formed is added to the powders which are granulated, if necessary, with an additional amount of water. The granulate is dried overnight at 35°, broken on a screen with 1.2 mm openings and compressed into tablets using concave punches, uppers bisected.

EXAMPLE 3

Anxiolytic formulations comprising e.g. 0.01–1.0% solutions in distilled water, as well as analogous formulations to those given in examples 1 and 2 and comprising 5 to 200 mg of certain compounds encompassed by U.S. Pat. No. 4,316,900, are prepared, i.e. with the active ingredient being:

(a)  7-chloro-2p-methyl-1,3,4,14b-tetrahydro-10H-pyrazino [1,2-a]pyrrolo[2,1-c][1,4]benzodiazepine mono-maleate, (b) 2-allyl-1,3,4,14b-tetrahydro-10H-pyrazino[1,2-a]pyrrolo[2,1-c][1,4]benzodiazepine mono-maleate, (c)  2-cyclopropylmethyl-1,3,4,14b-tetrahydro-10H-pyrazino[1,2-a]-pyrrolo[2,1-c][1,4]benzodiazepine mono-maleate, (d)  2-(2-acetoxyethyl)-1,3,4,14-b-tetrahydro-10H-pyrazino[1,2-a]pyrrolo[2,1-c][1,4]benzodiazepine mono-fumarate, (e)  2-(2-hydroxyethyl)-1,3,4,14b-tetrahydro-10H-pyrazino[1,2-a]pyrrolo[2,1-c]benzodiazepine mono-fumarate.

What is claimed is:

1. A method of treating anxiety in mammals comprising the enteral or parenteral administration to a mammal in need thereof of an effective amount of an anxiolytic compound or of an effective amount of a pharmaceutical composition comprising an anxiolytic compound of formula I

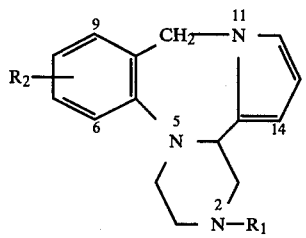

wherein $R_1$ is hydrogen, lower alkyl, lower alkenyl, cyclopropyl(lower)alkyl, lower alkanoyloxy(lower)alkyl or hydroxy-(lower)alkyl; $R_2$ is hydrogen, halogen or trifluoromethyl; or a pharmaceutically acceptable salt thereof, in combination with one or more pharmaceutical carriers.

2. A method according to claim 1 comprising the enteral administration of an anxiolytic compound as defined in claim 1 or a pharmaceutical composition comprising said compound.

3. A method according to claim 1 wherein, in said compound of formula I defined therein, $R_1$ is alkyl, alkenyl or hydroxyalkyl with up to 4 carbon atoms; and $R_2$ is hydrogen, chloro, fluoro or trifluoromethyl.

4. A method according to claim 1 wherein, in said compound of formula I defined therein, $R_1$ is methyl, allyl or hydroxyethyl; $R_2$ is hydrogen or 7-(chloro, fluoro or trifluoromethyl); and the pharmaceutically acceptable salt is the hydrochloride, maleate or fumarate salt thereof.

5. A method, according to claim 1, of treating anxiety in mammals comprising the enteral or parenteral administration to a subject in need thereof of an anxiolytic effective amount of 2-methyl-1,3,4,14b-tetrahydro-10H-pyrazino[1,2-a]pyrrolo[2,1-c][1,4]benzodiazepine or a pharmaceutically acceptable acid addition salt thereof, or of an anxiolytic effective amount of a pharmaceutical composition comprising said compound in combination with one or more pharmaceutical carriers.

6. A method according to claim 5 wherein the acid addition salt is the maleate salt.

7. A method according to claim 5 comprising the oral administration of a compound defined therein or of a pharmaceutical composition comprising said compound.

* * * * *